US011237639B2

(12) United States Patent
Alvarado et al.

(10) Patent No.: US 11,237,639 B2
(45) Date of Patent: Feb. 1, 2022

(54) METHOD AND SYSTEM FOR ELECTRONIC COMMUNICATION BY PERSONS WITH DISABILITIES

(71) Applicant: Iowa Adaptive Technologies, Inc., Coralville, IA (US)

(72) Inventors: Alexander S Alvarado, Harwood Heights, IL (US); Richard Ray Hurtig, Philadelphia, PA (US)

(73) Assignee: Iowa Adaptive Technologies, Inc., Coralville, IA (US)

( * ) Notice: Subject to any disclaimer, the term of this patent is extended or adjusted under 35 U.S.C. 154(b) by 0 days.

(21) Appl. No.: 16/366,113

(22) Filed: Mar. 27, 2019

(65) Prior Publication Data

US 2019/0302894 A1    Oct. 3, 2019

Related U.S. Application Data

(60) Provisional application No. 62/648,591, filed on Mar. 27, 2018.

(51) Int. Cl.
*G06F 3/01*    (2006.01)
*H04Q 9/02*    (2006.01)

(52) U.S. Cl.
CPC .............. *G06F 3/017* (2013.01); *G06F 3/015* (2013.01); *H04Q 9/02* (2013.01)

(58) Field of Classification Search
CPC . A61F 4/00; G06F 3/015; G06F 3/017; G06F 3/0346; H04Q 9/00; H04Q 9/02
See application file for complete search history.

(56) References Cited

U.S. PATENT DOCUMENTS

| | | |
|---|---|---|
| 6,163,281 A | 12/2000 | Torch |
| 7,369,951 B2 | 5/2008 | Blosser et al. |
| 7,515,054 B2 | 4/2009 | Torch |
| 7,639,146 B2 | 12/2009 | Baura |
| RE41,376 E | 6/2010 | Torch |
| 9,110,505 B2 | 8/2015 | Mastandrea, Jr. |
| 9,128,522 B2 | 9/2015 | Raffle et al. |
| 2010/0295781 A1* | 11/2010 | Alameh .................. G06F 3/017 345/158 |
| 2011/0080339 A1* | 4/2011 | Sun ....................... G06F 3/0346 345/157 |
| 2011/0167391 A1* | 7/2011 | Momeyer ............... G06F 3/038 715/863 |
| 2011/0260829 A1* | 10/2011 | Lee ........................ H04M 1/67 340/5.51 |
| 2012/0260220 A1* | 10/2012 | Griffin .................... G06F 3/017 715/863 |
| 2013/0027341 A1* | 1/2013 | Mastandrea ............ G06F 3/038 345/173 |
| 2013/0257709 A1 | 10/2013 | Raffle et al. |
| 2014/0375782 A1 | 12/2014 | Chichilnisky et al. |
| 2017/0011210 A1* | 1/2017 | Cheong ................... G06F 21/32 |
| 2018/0153430 A1* | 6/2018 | Ang ....................... A61B 5/053 |

\* cited by examiner

*Primary Examiner* — Omer S Khan
(74) *Attorney, Agent, or Firm* — Simmons Perrine Moyer Bergman PLC

(57) ABSTRACT

A method and system for detecting and using intentional gestures utilizing a six-axis inertial measurement unit (IMU) provides individuals with limited motor abilities the ability to control multiple devices. The system responds to small intentional gestures produced by any part of the user's body. Unlike existing game controllers and adapted mouse devices, the system has the ability to learn the unique kinematic characteristics of the user's gestures.

1 Claim, 8 Drawing Sheets

METHOD AND SYSTEM FOR ELECTRONIC COMMUNICATION BY PERSONS WITH DISABILITIES

CROSS REFERENCE TO RELATED APPLICATIONS

The present application claims the benefit of the filing date of provisional patent application having Ser. No. 62/648,591 filed on Mar. 27, 2018, by Iowa Adaptive Technologies, Inc., DBA as VOXELLO Inc., which application is incorporated herein in its entirety by this reference.

FIELD OF THE INVENTION

The present invention generally relates to assistance of physically limited patients with communication with care givers and other devices in their environment, and more particularly relates to methods and systems for detecting intentional gestures of persons with physical disabilities.

BACKGROUND OF THE INVENTION

In the past, patients in care facilities would use nurse call buttons and intercoms to summon assistance and would speak with the care provider upon arrival. Electronic tablets have been adapted with software interfaces to aid persons with interacting with electronic systems. Use of touch screen tablets with enlarged buttons and controls have been used successfully by person with motor skills albeit diminished.

While these patient touch screen tablets, and the like, have enjoyed much success over the years, many persons with more dramatic limitations have often been unable to interact with even these patient-adapted electronic computer systems. Voxello Inc. has developed the noddle system with a smart switch for accepting input from multiple sensors to provide augmentative and alternative patient communication. This noddle system has utilized sensors such as: 1) a microphone for picking up intentional tongue clicks, which can be adapted to even work with patients who are endotracheally intubated, 2) a touch sensor for tongue manipulation through a patient's cheek; and 3) a touch sensor placed on bedding to detect gross motor movements. Some systems have proposed using cameras for detection of eye movement, etc.

While systems have increased the number of patients who are able to effectively communicate and interact with caregivers and their environment, still many patients remain unable to perform the specific gestures detected by these sensors.

Consequently, there exists a need for improved methods and systems for detecting intentional patient gestures and utilizing the same in an effective manner.

SUMMARY OF THE INVENTION

It is an object of the present invention to increase the number of patients who are capable of interacting with electronic computer and communication systems.

It is a feature of the present invention to utilize a sensor that is designed to detect intentional gestures which are defined by movement back and forth from a starting position along or about a particular axis.

It is another feature of the present invention to provide a sensor with an ability to learn characteristics of a specific patient's gesture such as speed of a gesture and magnitude of movement.

It is yet another feature of the present invention to permit this sensor to be utilized at countless positions on the patient's body, depending upon the individual patient's abilities.

It is an advantage of the present invention to expand the scope of movements that can be recognized as intentional gestures.

The present invention is carried out in an environment of reduced physical constraints, in a sense that motions which are detected as intentional gestures are not directed in advance at a particular part of the body, instead utilizes the recognition that intentional gestures, irrespective of the body part involved, have certain similar characteristics.

Accordingly, the present invention is a method of detecting intentional gestures, comprising the steps of:

A method of improving operation of patient communication systems by persons with physical limitations, comprising the steps of:

providing an inertial measurement unit (IMU) 304 configured to be coupled to a body portion of a human patient;

moving said IMU 304 by moving said body portion;

analyzing an electrical output of said IMU 304 which corresponds to a measurement of said step of moving said IMU 304 by moving said body portion;

issuing a declaration that said step of moving said IMU 304 by moving said body portion was an intentional gesture based upon a determination that said electrical output represents a motion of said IMU 304 away from a starting location followed by a motion back toward said starting location; and using said declaration to provide input into a patient communication system.

Additionally, the present invention is an improved system for detecting intentional patient gesture's comprising:

An intentional gesture detection system for providing input into a patient communication system, the intentional gesture detection system comprising:

an electrocardiogram (ECG) electrode 210, with adhesive thereon coupled with a body part of a person with physical limitations;

a sensor body 202, coupled to said ECG electrode 210;

an inertial measurement unit (IMU) 304, disposed in said sensor body 202;

said IMU 304 being configured to generate electronic output, representative of motion, when said body part is moved;

a microcontroller 302;

a communication interface 306 electrically coupled between said IMU 304 and said microcontroller;

a sensor wired interface 204; coupled to said microcontroller 302; and said microcontroller 302 being configured to issue a declaration on said sensor wired interface 204 in response to receipt of said electronic output which represents a motion of said IMU 304 away from a starting location followed by a motion back toward said starting position.

BRIEF DESCRIPTION OF THE DRAWINGS

The invention may be more fully understood by reading the following description of the preferred embodiments of the invention, in conjunction with the appended drawings wherein.

DETAILED DESCRIPTION

Although described with particular reference to patients, the systems and methods of the present invention can be implemented to aid many different types of persons with limitation irrespective of their location and care level.

In an embodiment, the system and method of the present invention described herein can be viewed as examples of many potential variations of the present invention which are protected hereunder. The following details are intended to aid in the understanding of the invention whose scope is defined in the claims appended hereto.

Figure 1:
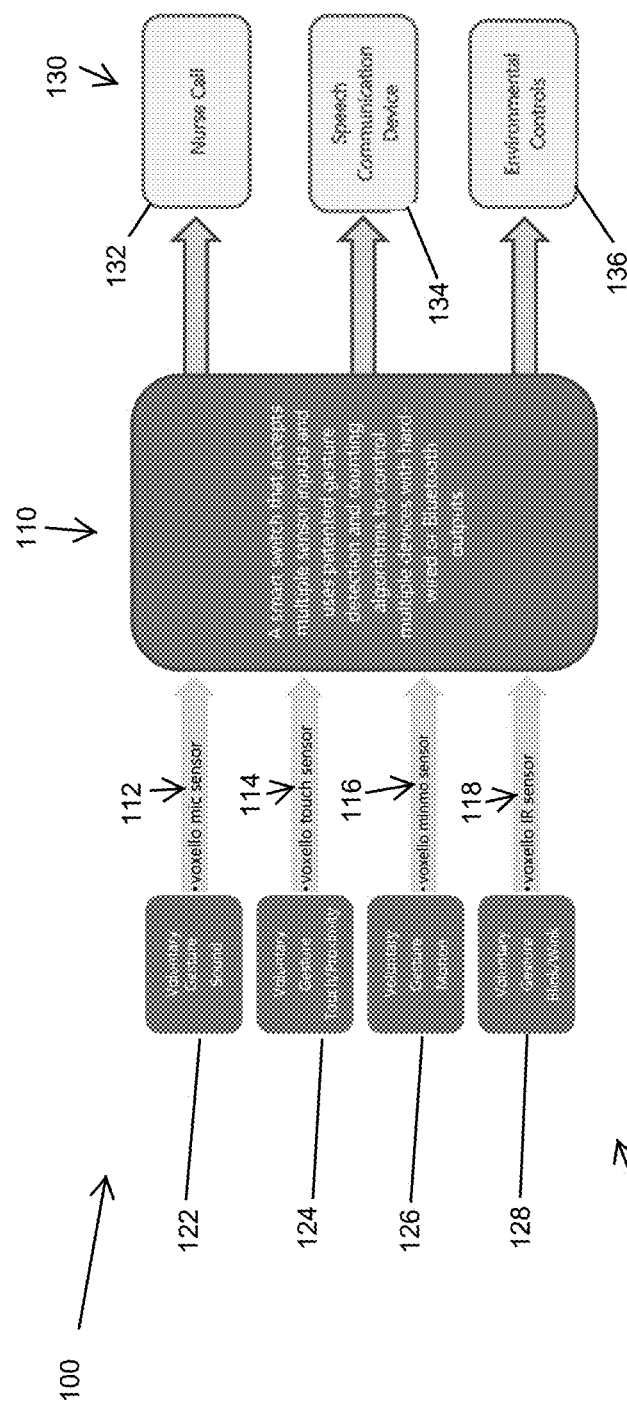
FIG. 1 is a functional block diagram view of the system incorporating the present invention.

Now referring to the drawings wherein like numerals refer to like matter throughout, and more particularly in FIG. 1, there is shown a conceptual view of the overall system and method of the present invention, generally designated 100.

The center of the system 100 is smart switching controller 110, such as the noddle which is commercially available from Voxello, Inc. at www.voxello.com.

Smart switching controller 110 in combination with an assortment of sensors including microphone sensor 112, touch sensor 114, minmo sensor 116, and IR sensor 118. With each of these sensors 112, 114, 116 and 118 there is a corresponding gesture sound gesture 122, touch gesture 124, motion gesture 126 and wink gesture 128, respectively. The patient makes the assortment 120 of gestures to be detected and the system provides instruction to assortment 130 of electronic equipment including nurse call system 132, speech communication device 134, and environmental controls 136.

The minmo sensor 116 is a new addition to the assortment of sensors previously used and offered for sale by Voxello.

By way of background, smart switching controller 110, aka "the noddle" was designed to provide individuals who are physically limited with the ability to summon help (e.g. nurse call system 132), effectively communicate (e.g. control a speech communication device 134) and also control environmental controls 136 (e.g. lights, fans). Many hospitalized patients or individuals with long standing physical disabilities do not have the ability to activate conventional nurse call buttons or use touch screen devices. The noddle, smart switching controller 110, was designed to detect the smallest intentional gesture that patients can make (e.g. an audible tongue click, a wink, a small head or shoulder movement). It accepts input from a range of sensors and uses patented gesture detection and counting algorithms to allow the user who might only be able to produce a small voluntary gesture to control multiple devices. The smart switching controller 110 autodetects the type of sensor being used and applies the appropriate processing algorithm. The smart switching controller 110 counts the number of sequential gestures detected and based on that number controls one of the smart switching controller 110 outputs which can be linked via hardwired or Bluetooth connection to activate one or more of the assortment 130 of electronic equipment.

Voxello designed the noddle to serve the widest range of individuals and has designed a range of sensors that can be easily interchanged. No individual sensor is expected to work with everyone. The microphone sensor 112 is designed to respond to small audible tongue clicks. The touch sensor 114 is a proximity sensor that can detect small low force gestures such as a small finger or tongue movement.

The minmo sensor 116 expands the types of voluntary gestures (e.g. small head nod, shoulder shrug, wrist rotation or foot tap) that can be used by the noddle. A unique characteristic of this sensor is its ability to learn the characteristics of the user's gesture (e.g. extent and speed of the gesture).

The minmo sensor 116 is a noddle-compatible sensor capable of capturing human gestures to control a nurse call system 132, a speech communication device 134 and environmental controls 136. The minmo sensor 116 can be mounted to an individual on anatomical locations including, but not limited to, the head, shoulder, wrist and foot. The minmo sensor 116 actively runs a gesture detection algorithm on the constantly streamed movement data that is acquired through a six-axis Inertial Measurement Unit (IMU) 304. Upon detection of a part of a gesture or a full gesture, the minmo sensor 116 will relay a signal to the noddle indicating what has been performed.

Figure 2:
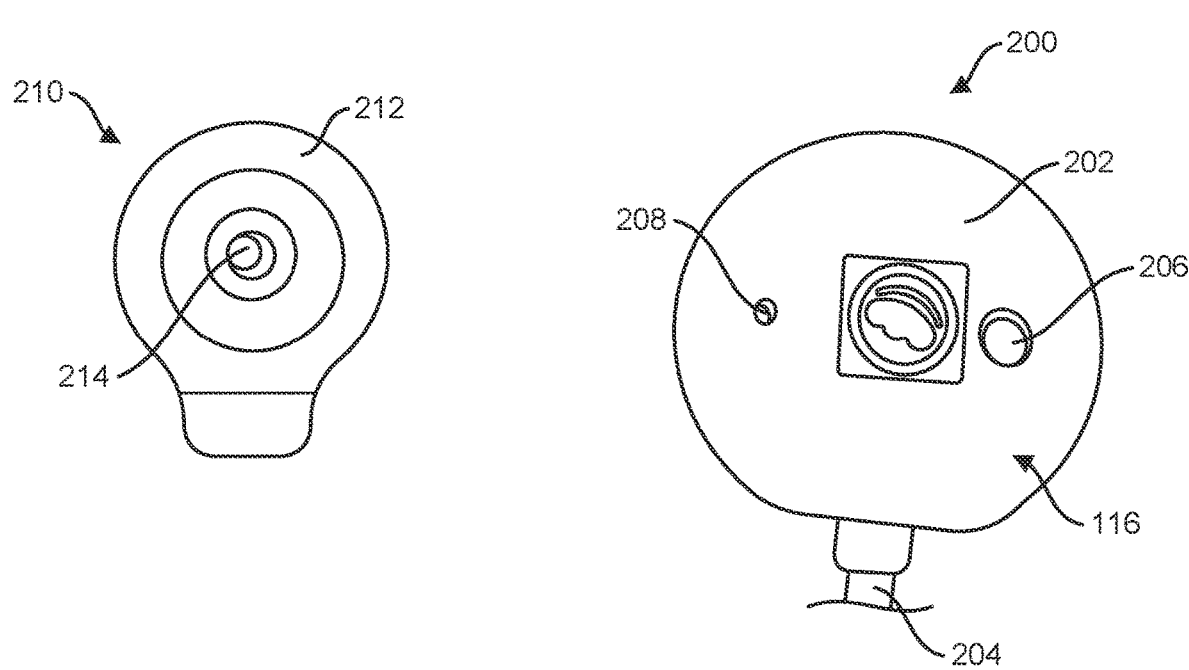
FIG. 2 is an image of the minmo sensor 116 of FIG. 1 with a representative mount.

Now referring to FIG. 2 there are shown image of the minmo sensor 116 which includes a minmo sensor body 202, a minmo sensor wired interface 204, minmo selector button 206, and LED 208 along with a separate minmo mount 210 which includes a minmo mount adhesive substrate 212 and a minmo mount connector 214. Minmo mount 210 can be a prior art electrode used in ECGs to couple to a patient's skin.

Figure 3:
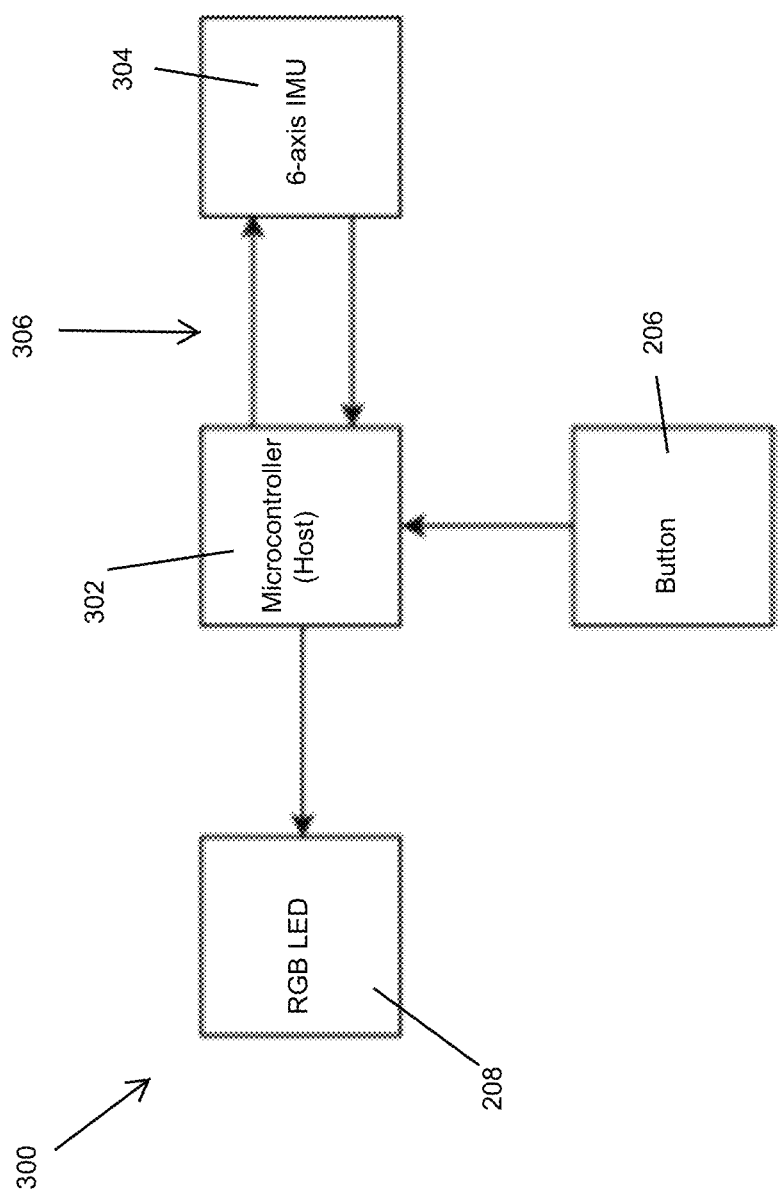
FIG. 3 is hardware block diagram of the major electronic components of the minmo sensor of FIG. 1.

Now referring to FIG. 3, there is shown a block diagram of the hardware components of the minmo sensor 116 which include a RGB LED (red-green-blue light-emitting diode) 208, a minmo host microcontroller 302 which is coupled to a six-axis inertial measurement unit (IMU) 304 by a four-wire Serial Peripheral Interface (SPI) connection 306. The minmo selector button 206 is also shown. Minmo sensor 116 also includes additional and various passive components, not shown in this simplified block diagram.

Figure 4:
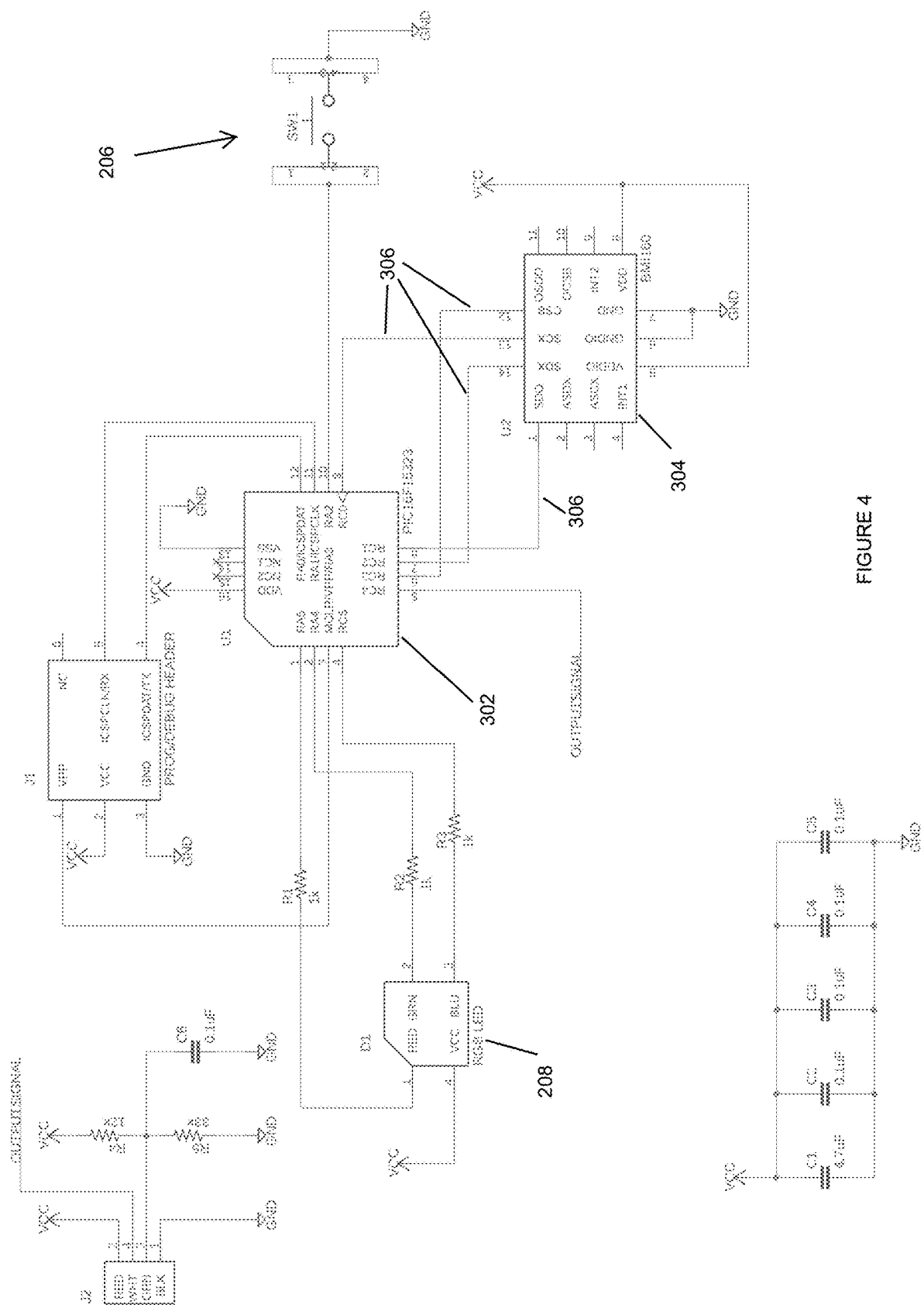
FIG. 4 is a detailed electronic circuit of the minmo sensor of FIG. 1.

The details of the hardware design including these additional passive components can be best understood by now referring to FIG. 4, which provides much more detail.

The minmo host microcontroller 302 can execute software and process data from the inertial measurement unit 304, as well as monitors the minmo selector button 206 and control the LED functions of minmo selector button 206. The IMU 304 and microcontroller 302 relay information over the four-wire Serial Peripheral Interface (SPI) connection 306.

Figure 5:
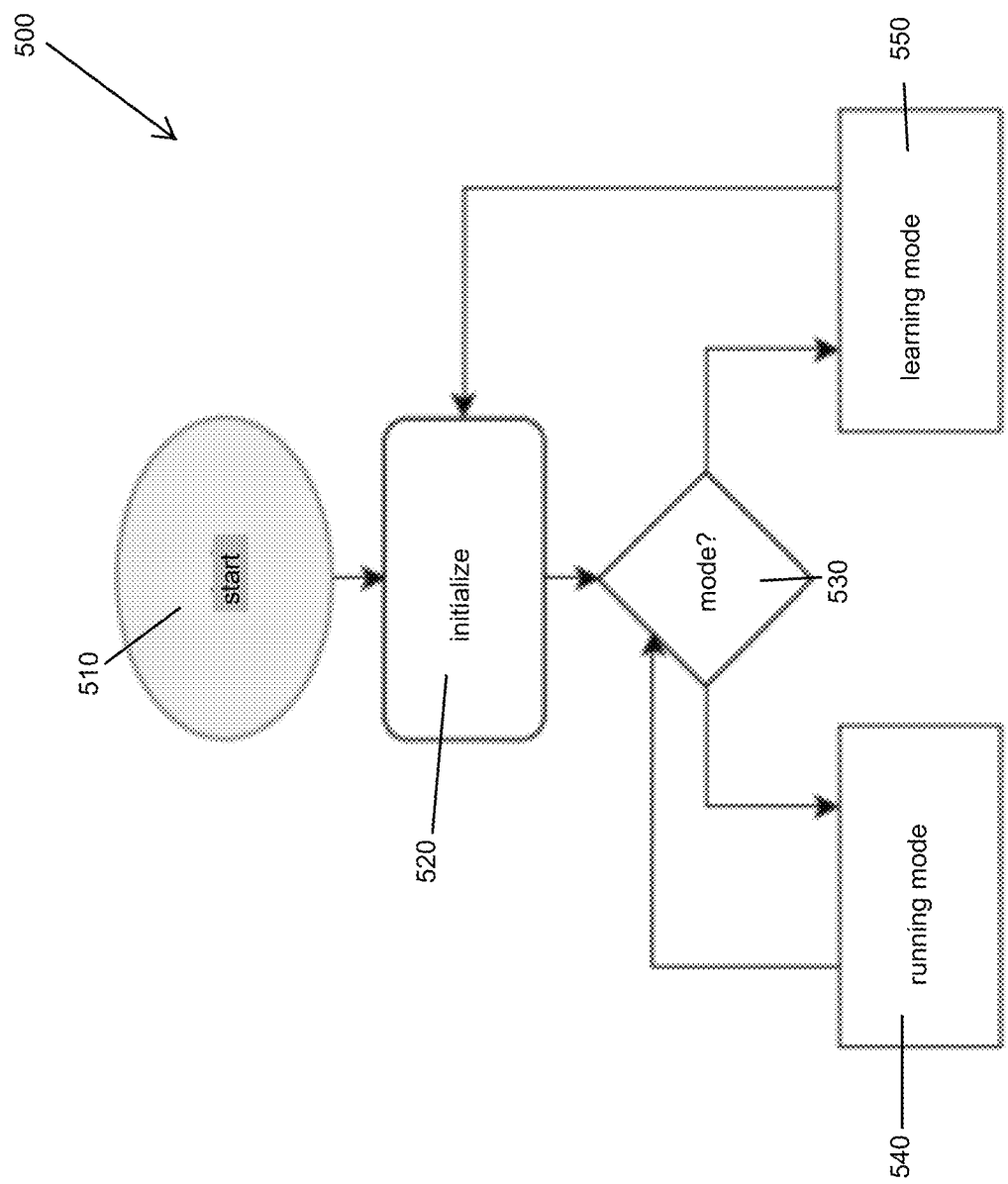
FIG. 5 is a high-level software flow diagram of the operation of the minmo sensor 116 of FIG. 1
Figure 6:
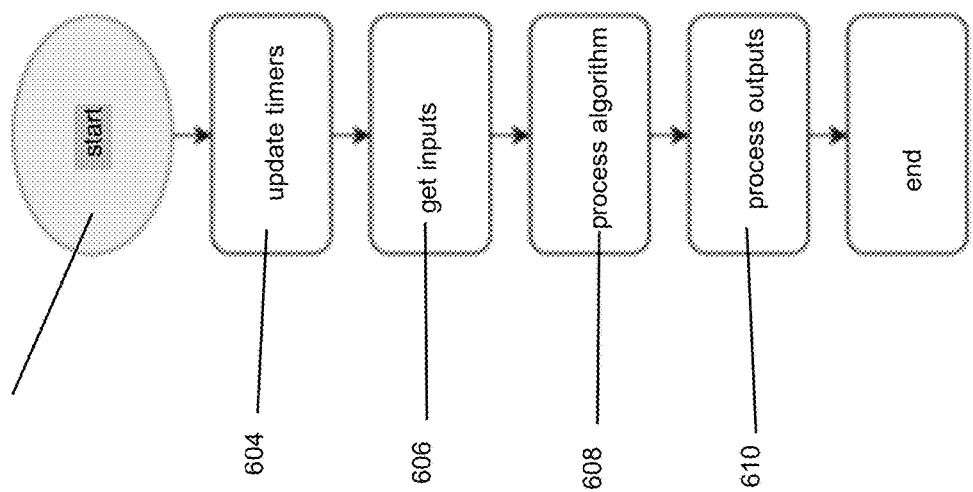
FIG. 6 is a more detailed software flow diagram of the running mode 540 of FIG. 5.
Figure 7:
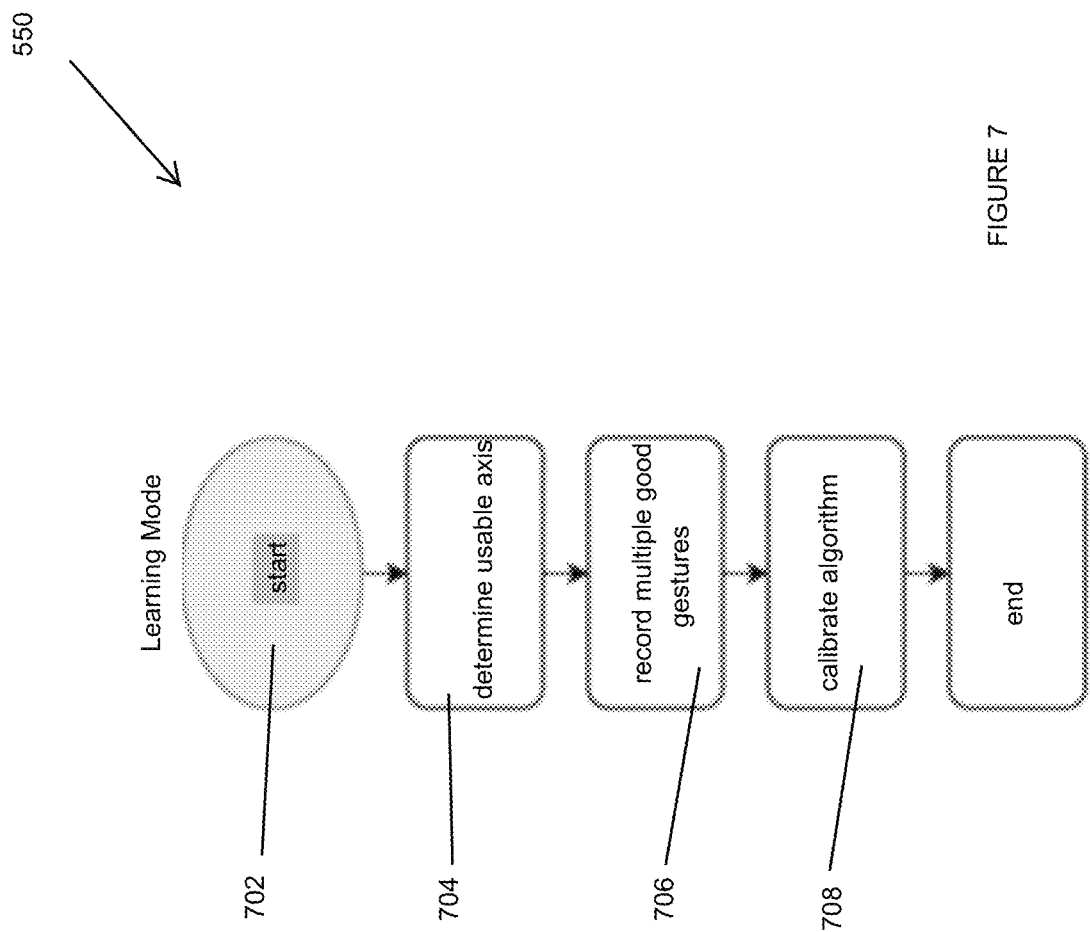
FIG. 7 is a more detailed software flow diagram of the learning mode 550 of FIG. 5.

Now referring to FIGS. 5, 6 and 7, there is shown simplified diagrams of the software of the minmo sensor 116 functions. When the minmo sensor 116 is powered on during the minmo operational start 510 step, the microcontroller 302 will run an initialize step 520 to set up required peripherals including internal oscillator, watch dog timer, digital inputs and output pin setup, analog inputs, pull up resistor enables, timer module, pin mapping using peripheral pin select (PPS), peripheral module (PM) enable, interrupt enable, Universal Asynchronous Receiver Transmitter (UART) enable, Serial Peripheral Interface (SPI) enable and initialization of the IMU. Once the microcontroller and IMU are initialized, an operational mode selection 530 startup sequence is executed that flashes the LED and sets running mode 540. Running mode 540 is in normal operation whether or not learning mode 550 is enabled. The learning mode 550 loop is for calibrating the minmo sensor 116; once learning mode 550 has been executed (running to determine usable axis 704 step, record multiple good gestures step 706 and calibrate algorithm 708), the microcontroller 302 initializes a soft reset and then continues to running mode 540.

Now referring to FIG. 6, more detail is provided for the Running mode 540 which executes six functions that work together to make the sensor 116 operate as intended.

The main running mode 540 function is an infinite loop that runs six functions which make the minmo sensor 116 work. If the sensor 116 has power, these functions will run. These functions are at the top of the hierarchy and most of them call several sub-functions that allow them to complete their tasks. Each function and a brief description of what they do is summarized as follows:

timer( )—keeps time, allows sensor to operate in a synchronous manner, see update timers step 604;

process_hmi( )—constantly checks the human machine interface (the button) see get inputs step 606;

quantify_data( )—makes quantifications of the data to be analyzed by the gesture algorithm; see get inputs step 606;

process_data_algorithm( )—runs the desired gesture algorithm on the calculated quantification, see process algorithm 608 step;

innervate_rgb_led( )—controls the LED feedback to the user depending on the state of the sensor, see process algorithm 608 step;

process_output—controls the output pin to the noddle, see process outputs 610 step;

These functions all call subroutines to accomplish their intended goals.

The functions 'quantify_data( )' and 'process_data_algorithm( )' compose the gesture searching algorithm. Quantify_data( ) filters the data, then sends it to three main sub-functions that are able to detect when certain events happen in the incoming data.

Figure 8:
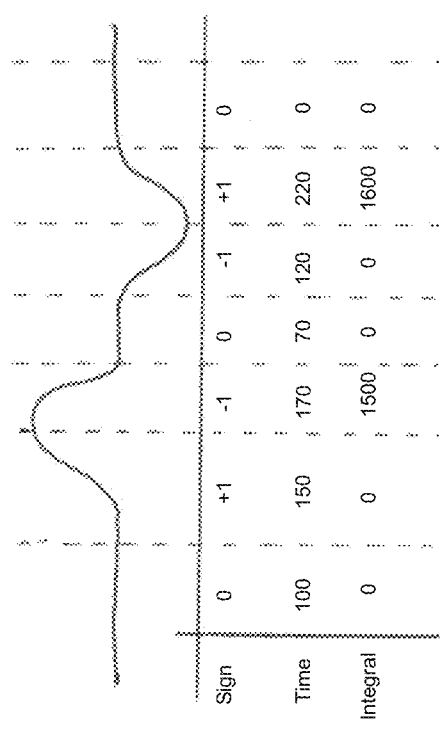
FIG. 8 is a depiction of an ideal gesture.

Now referring to FIG. 8 that characterizes an ideal (or "perfect") gesture and can be used to visualize what the algorithm is doing.

The first main sub-function detects the sign. As shown in FIG. 8, when data is increasing, the sign is positive '1' and when the data is decreasing the sign is '−1'. When no motion is occurring, the sign is '0'. The sign is zero ('0') when motion is below a certain threshold that is pre-defined in software to be approximately 2.5 to 5 RPM.

The second main sub-function measures the length of time that each sign occurs. This timing is primarily used to filter out movements that are very short and to determine the periods of time between peaks within the data.

The third main sub-function integrates the peaks to give a quantification of the magnitude of the motion performed. This information is very important in determining whether or not a motion that occurred was a gesture. A gesture must be roughly a 'to-fro' or 'there-and-back' motion; therefore, if these integral values are roughly equal and opposite in sign, it would indicate that two successive movements that just occurred were in fact an intentional gesture in combination.

Three versions of software were developed based on these main features and some perform better than others. They are summarized and described, in general, as follows.

Revision A1

This version of software is highly constrained and does not allow for a continuous capture of motion data. It must see a pre-defined period of no movement before any gesture happens as well as a very specific sequence of data as well as a pre-defined period of no movement after the gesture. This structure allows massive amounts of movement to be completely ignored. This software version has trouble with motions that are not ideal or "perfect" which led to the development of revision A2.

Revision A2

This version of code eliminated the need for pauses before and after gestures and allowed for much faster control of the sensor. Each sub-function, sign, time and integral all store data in arrays referred to as "buffers". In revision A2, the buffers only contained enough space to store one (1) gesture at a time. In this revision, the buffers were expanded to be capable of containing four (4) entire gestures. The gesture algorithm would then be able to actively search the buffers when a new piece of data came into the buffers. The most concerning issue with this version was that it looked for a 'sign sequence.' Referring back to FIG. 8, the perfect data had a sign sequence of the following: 0, +1, −1, 0, −1, +1, 0. This sequence indicated that a positive peak and then a negative peak had occurred. There is another possible sign sequence which is a negative then a positive peak: 0, −1, +1, 0, +1, −1, 0. This pre-defined sign sequence was a problem when the data was not ideal or "perfect", and small tremors were introduced into the recorded motion. Sign sequences like "0, +1, −1, +1, −1, 0, −1, +1, 0" would occur and be ignored due to an invalid sign sequence. Two peaks still occurred, and their integral values were often very similar, but the gesture algorithm did not recognize them as a real gesture because of the contradicting sign sequence. This problem was addressed in revision A3.

Revision A3

This version of code is very similar to revision A2. However, it no longer logs signs; instead, it only integrated the peaks to get a quantification of the magnitude and distance traveled during the movement. This method is efficient at identifying gestures even if the movement is not ideal or "perfect" by ignoring the sign sequence and only comparing the integrations of the peaks of the recorded movement.

The above description of the software is capable of functioning while using just one axis of rotation sensed by the gyroscope. Ideally, the present invention would be expanded to use all gyroscope axes as well as all axes of the accelerometer. This could dramatically increase the range of possibly acceptable gestures that a patient might produce. Many patients can have difficulty performing a particular gesture that is accepted by the system as being a recognized gesture. The use of all three rotational axes and all three linear axes can essentially allow the sensor to respond to unique gestures that a patient can easily and comfortably produce. This would greatly increase the potential for positive gesture recognition results coming from the learning mode.

The present invention provides four different output pulses which help distinguish it from gaming controllers and worn devices such as a cursor controlling mouse.

The present invention provides an output pulse at the beginning and end of each gesture and as well as when entering and leaving learning mode. This distills continuous motion data into discrete gestures.

The embodiment of the present invention when configured to monitor all six axes for movement will permit the recording of much more data during the learning mode which permits the ability to recognize gestures which may not be recognizable if only one axis is monitored for motion. The ability to detect the unique gestures that patients can easily and comfortably produce is dramatically improved with the logical expansion to detecting motion with respect to all six axes.

A further benefit of the learning mode that utilizes the six axes data is that it would allow for learning and responding to more than one unique gesture. Each learned gesture could then be associated with a particular output function from the noddle smart switch. The independence of the gestures further distinguishes the present inventions from the fixed axes constraints of gaming controllers and worn devices such as a cursor controlling mouse.

The precise implementation of the present invention will vary depending upon the particular application.

It is thought that the method and apparatus of the present invention will be understood from the foregoing description and that it will be apparent that various changes may be made in the form, construct steps and arrangement of the parts and steps thereof without departing from the spirit and scope of the invention or sacrificing all of their material advantages. The form herein described is merely a preferred and/or exemplary embodiment thereof.

We claim:

1. A method of improving operation of patient communication systems by persons with physical limitations, comprising the steps of:
    providing an inertial measurement unit (IMU) configured to be coupled to a body portion of a human patient;
    moving said IMU by moving said body portion;
    analyzing an electrical output of said IMU which corresponds to a measurement of said step of moving said IMU by moving said body portion;
    without utilizing any stored gesture information which existed before said step of moving said IMU by moving said body portion, making a determination that said electrical output represents a three dimensional motion of said IMU away from a starting location followed by a three dimensional motion back toward said starting location;
    issuing a notification that said step of moving said IMU by moving said body portion was an intentional gesture based upon said determination that said electrical output represents a three dimensional motion of said IMU away from a starting location followed by a three dimensional motion back toward said starting location;
    using said notification to provide input into a patient communication system;
    providing a buffer sized and configured to store data resulting from a plurality of gestures;
    wherein said step of issuing a notification is based upon a determination that said plurality of gestures have occurred where each gesture of said plurality of gestures includes said three dimensional motion away from said starting location followed by a motion back toward said starting location;
    wherein the buffer store data resulting from said plurality of gestures without a pause in motion between said plurality of gestures;
    wherein said motion of said IMU away from a starting location is a rotational motion around a first axis;
    wherein said IMU is a six axis IMU with three gyroscopes and three accelerometers, and further comprising a host microcontroller which in combination are configured, together with said buffer, to permit learning of a plurality of unique learned gestures each of which are associated with a different predetermined output signal;
    wherein said determination that said plurality of gestures have occurred is based upon an integration of a plurality of peaks in an output signal from said IMU so as to get a quantification of a magnitude and distance traveled during any movement which resulted in said plurality of peaks;
    coupling an electrocardiogram (ECG) electrode to said body portion in a gap between said body portion and said IMU;
    providing a sensor body for containing therein said IMU and said microcontroller; and
    coupling said sensor body to said ECG electrode.

* * * * *